United States Patent
Nagy et al.

(10) Patent No.: US 7,763,601 B2
(45) Date of Patent: Jul. 27, 2010

(54) PREVENTION AND TREATMENT OF OBESITY

(75) Inventors: Péter Literáti Nagy, Budapest (HU); Zoltán Szilvássy, Debrecen-Józsa (HU); Kálmán Tory, Budapest (HU); László Vígh, Szeged (HU); Kálmán Takács, Budapest (HU); József Mandl, Budapest (HU); Balázs Sümegi, Pécs (HU); Sándor Bernáth, Telki (HU); Attila Kolonics, Budapest (HU); Gábor Balogh, Szeged (HU); János Egri, Budapest (HU)

(73) Assignee: N-Gene Research Laboratories, Inc., New York, NY (US)

(*) Notice: Subject to any disclaimer, the term of this patent is extended or adjusted under 35 U.S.C. 154(b) by 0 days.

(21) Appl. No.: 11/687,945

(22) Filed: Mar. 19, 2007

(65) Prior Publication Data

US 2008/0108673 A1    May 8, 2008

Related U.S. Application Data

(60) Provisional application No. 60/856,117, filed on Nov. 2, 2006.

(51) Int. Cl.
*A61K 31/33* (2006.01)
*A61K 31/155* (2006.01)
*A61P 3/04* (2006.01)

(52) U.S. Cl. ............... 514/183; 514/633; 514/909

(58) Field of Classification Search .............. None
See application file for complete search history.

(56) References Cited

U.S. PATENT DOCUMENTS

| | | | |
|---|---|---|---|
| 4,187,220 | A | 2/1980 | Takacs et al. |
| 6,306,878 | B1 | 10/2001 | Sumegi |
| 6,440,998 | B1 | 8/2002 | Sumegi |
| 6,451,851 | B1 | 9/2002 | Sumegi |
| 6,458,371 | B1 | 10/2002 | Farkas et al. |
| 6,656,955 | B2 | 12/2003 | Sumegi |
| 6,720,337 | B2 | 4/2004 | Sumegi |
| 6,838,469 | B2 | 1/2005 | Sumegi |
| 6,884,424 | B2 | 4/2005 | Farkas et al. |

FOREIGN PATENT DOCUMENTS

| | | |
|---|---|---|
| WO | WO 00/07580 | 2/2000 |
| WO | WO 03/007951 | 1/2003 |
| WO | WO 2005/122678 | 12/2005 |
| WO | WO 2005/123049 | 12/2005 |
| WO | WO 2006/079910 | 8/2006 |
| WO | WO 2008/030891 | 3/2008 |
| WO | WO2008/030891 A2 * | 3/2008 |

OTHER PUBLICATIONS

Szabados et al., BGP-15, a Nicotinic Amidoxime Derivate Protecting Heart from Ischemia Reperfusion Injury through Modulation of Poly(ADP-ribose) Polymerase, 2000, Biochemical Pharmacology, vol. 59, pp. 937-945.*
Merriam-Webster OnLine Dictionary, "Prevent", downloaded from http://www.merriam-webster.com/dictionary/prevent, accessed Apr. 7, 2008, pp. 1 of 1.*
The Merck Manual, "Obesity: Disorders of Nutrition and Metabolism", downloaded from http://www.merck.com/mmhe/print/sec12/ch156/ch156a.html, accessed Apr. 9, 2008, pp. 1-8 of 8.*
Blin, "A Comparative Review of New Antipsychotics," *Can. J. Psychiatry*, 44(3):235-244 (1999).
Ruetsch et al., "Psychotropic drugs induced weight gain: a review of the literature concerning epidemiological data, mechanisms and management," *L'Encéphale*, 31:507-516 (2005) (English abstract).
Alexander Burkle, FEBS Journal 272 (2005) 4576-4589.
Olga Ilnytska et al., Diabetes 55 (2006) 1686-1694.
Thomas M. Loftus et al., Science 288 (2000) 2379-2381.
Bruno Sepodes et al., Medical Science Monitor, (2003) 9(S1): 61-0.
Eszter Szabados et al., Biochemical Pharmacology 59 (2000) 937-945.
www.merriam-webster.com/dictionary/prevent, accessed Apr. 7, 2008, p. 1 of 1.
Obesity: Disorders of Nutrition and Metabolism: Merck Manual Home Edition: Ch156:1-8, 2003.
Zhao-Qi Wang, Genes & Development 11 (1997) 2347-2358.
Berthoud, H.R., "Mind versus metabolism in the control of food intake and energy balance" Physiol. Behav. 81:781-793, 2004.
Flier, J.S., "Clinical Review 94: What's in a name? in search of leptin's physiologic role" J. Clin. Endocrinol. Metab. 83:1407-1413, 1998.
Leibel, R.L., "The role of leptin in the control of body weight" Nutr. Rev. 60:S15-S19, 2002.

\* cited by examiner

*Primary Examiner*—Ardin Marschel
*Assistant Examiner*—Gregg Polansky
(74) *Attorney, Agent, or Firm*—Fish & Richardson P.C.

(57) ABSTRACT

O-(3-piperidino-2-hydroxypropyl)-nicotinic amidoxime (BGP-15) or a pharmaceutically suitable acid addition salt thereof can be used for the prevention or reduction of weight gain or the reduction of the rate of body weight gain.

3 Claims, No Drawings

PREVENTION AND TREATMENT OF OBESITY

RELATED APPLICATION INFORMATION

This application claims priority to U.S. provisional application Ser. No. 60/856,117, filed Nov. 2, 2006.

BACKGROUND

Overweight and obesity represent the prevalent nutritional problem in the developed countries. According to World Health Organization estimates, more than 300 million adults are obese worldwide. In general, energy intake exceeding energy expenditures for a longer time results in abnormal body weight gain leading, at first, to overweight, later, obesity. In case of adults, overweight is characterized by a body mass index of 25-30 kg/m$^2$, while a body mass index of above 30 kg/m$^2$ indicates obesity.

Food intake and energy expenditure are normally matched over time. The biological system that controls energy homeostasis evolved, principally, to protect against weight loss during times of limited nutrient availability rather than weight gain during periods of food excess. Inherent biological defense against weight gain such as that conveyed by an elevated plasma level remained relatively undeveloped. [Leibel R. L.: The role of leptin in the control of body weight, Nutr. Rev., 60, S15-S19, discussion: S68-S87; Flier J. S., Clinical review 94: What's in a name? In search of leptin's physiologic role. J. Clin. Endocrinol. Metab., 83, 1407-1413, (1998); Berthoud H. R.: Mind versus metabolism in the control of food intake and energy balance, Physiol. Behav., 81, 781-793 (2004).]Therefore, once adaptive gene variants are implicated in weight gain when they are expressed in individuals living in an obesigenic environment, e.g., one that is characterized by ready availability of highly palatable, energy-rich foods and by minimal demand for physical activity. On the same way, insufficient or defective adiposity feedback signaling by hormones such as leptin can contribute to common forms of obesity. Thus, weight gain under certain nutrient load that is compensated in normal individuals can be referred to as pathological or abnormal weight gain.

Overweight and obesity are associated with hypertension and abnormal metabolic changes such as insulin resistance and dyslipidemia which are risk factors for diabetes. Obesity (particularly abdominal obesity), insulin resistance and dyslipidemia are major features of "pre-diabetes" (metabolic syndrome) that leads to Type 2 diabetes mellitus. Diabetes is accompanied by increased mortality due to a greater risk of cardiovascular disease. Thus, it can be stated that obesity predisposes to diseases of high risk such as Type 2 diabetes mellitus, cardiovascular diseases, osteoarthritis, formation of gall stones and various malignant diseases.

O-(3-piperidino-2-hydroxy-1-propyl)-nicotinic amidoxime) (abbreviated as BGP-15) was patented in 1976 as a new compound useful in the treatment of diabetic angiopathy, a complication of diabetes resulting in the damage of blood vessels (see, e.g., U.S. Pat. No. 4,187,220). The structure of BGP-15 is shown below.

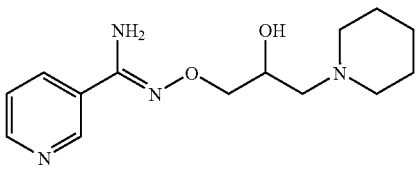

U.S. Pat. No. 6,306,878 refers to a method for the protection of the mitochondrial genome and/or mitochondrion from damage leading to myopathies and neurodegenerative diseases which comprises administering an effective non-toxic dose to a patient susceptible to such damage of an amidoximic acid derivative including BGP-15. A preferred myopathy is cardiomyopathy. Neurodegenerative diseases include Parkinson's disease, Huntington's disease and amyotrophic lateral sclerosis.

U.S. Pat. No. 6,458,371 refers to a composition comprising 0.1-30% of a hydroximic acid derivative including BGP-15 as the active ingredient and a carrier that is in the form of a cream, lotion, foam or spray. The composition is suitable for reducing the incidence of photodamage by radiation with UV-B.

U.S. Pat. No. 6,884,424 refers to a method for preventing actinic keratosis by applying a hydroximic acid derivative including BGP-15 to the affected skin surface.

U.S. Pat. No. 6,451,851 refers to a method of treating a patient suffering from a viral infection comprising administering to the patient a pharmaceutically effective amount of a known antivirally active agent together with a hydroximic acid derivative including BGP-15.

U.S. Pat. No. 6,440,998 refers to a pharmaceutical composition having antitumor activity with reduced side effect comprising cisplatin or carboplatin and a hydroximic acid derivative including BGP-15.

U.S. Pat. No. 6,656,955 refers to a pharmaceutical composition having antitumor activity with reduced side effect comprising paclitaxel or docetaxel and a hydroximic acid derivative including BGP-15.

U.S. Pat. No. 6,720,337 refers to a pharmaceutical composition having antitumor activity with reduced side effect comprising oxaliplatin and a hydroximic acid derivative including BGP-15.

U.S. Pat. No. 6,838,469 refers to a pharmaceutical composition having antitumor activity with reduced side effect comprising pyrimidine derivatives and BGP-15.

PCT Patent Application WO 00/07580 disclosed experimental data for the antidiabetic effect of BGP-15 in the treatment of type 1 diabetes mellitus. It is to be noted that type 1 diabetes mellitus is an autoimmune disease occurring at young age, while type 2 diabetes mellitus is a metabolic disease occurring at higher age.

PCT Application WO 03/007951 refers to a pharmaceutical combination of hydroximic acid derivatives including BGP-15 and an antidiabetic or anti-hyperlipidemic active agent for the prevention or treatment of a prediabetic state, metabolic X-syndrome or diabetes mellitus as well as disorders which are associated with the states listed above, namely endogenic metabolic disorders, insulin resistance, dislipidemia, alopecia, diffuse effluvium and/or female endocrine disorders based on androgenic preponderance. In the description, laboratory data indicate that BGP-15 enhances, synergistically, the effect of the known antidiabetic agent metformin and troglitazone, respectively. The laboratory data also show that BGP-15 in itself enhances the insulin sensitivity (thus, reduces the insulin resistance) in both normal and hyper-cholesterolemic animals relative to the control.

PCT Application WO 2005/122678 refers to the use of BGP-15 in a pharmaceutical composition having prokinetic effect (i.e. induces activity in the stomach and intestines. Prokinetic effect includes possible treatment of reflux esophagitis, gastroparesis, influencing bile flow from the gall bladder etc.

PCT Application WO 2005/123049 refers to the use of BGP-15 for mitochondrial genesis, i.e., to increase the number of mitochondria in the cells resulting in a roborating effect.

PCT Application WO 2006/079910 refers to the use of BGP-15 for the treatment of lesions in the oral cavity, especially periodontal disease.

SUMMARY

It has been found that O-(3-piperidino-2-hydroxypropyl)-nicotinic amidoxime or a pharmaceutically suitable acid addition salt thereof can be used for the prevention or reduction of excessive body weight or obesity in a patient.

Described herein are methods for the, prevention of abnormal body weight gain or treatment of or reduction of excessive body weight or obesity which comprises administering to a patient susceptible to abnormal body weight gain or having excessive body weight or beingobese an effective, non-toxic dose (or a composition comprising, consisting essentially of) of O-(3-piperidino-2-hydroxy-1-propyl)-nicotinic amidoxime or a pharmaceutically acceptable acid addition salt thereof. In various embodiments: O-(3-piperidino-2-hydroxy-1-propyl)-nicotinic amidoxime dihydrochloride is administered; a composition comprising of O-(3-piperidino-2-hydroxy-1 -propyl)-nicotinic amidoxime or a pharmaceutically acceptable acid addition salt thereof and a pharmaceutically acceptable carrier is administered. Also described is a method for reducing body weight gain or the rate of body weight gain in subject, the method comprising administering to the subject an effective, non-toxic dose of O-(3-piperidino-2-hydroxy-1-propyl)-nicotinic amidoxime or a pharmaceutically acceptable acid addition salt thereof (or composition comprising O-(3-piperidino-2-hydroxy-1-propyl)-nicotinic amidoxime or a pharmaceutically acceptable acid addition salt thereof):

In certain embodiments: the subject is not suffering from Type 2 diabetes; the O-(3-piperidino-2-hydroxy-1-propyl)-nicotinic amidoxime or a pharmaceutically acceptable acid addition salt thereof is not administered together with an anti-diabetic or anti-hyperlipidemic agent; the subject is not being treated with anti-diabetic or anti-hyperlipidemic agent (e.g., the subject is not being treated with metformin or troglitazone); the subject is not being treated with exogenous insulin; the subject has a body mass index greater than 25 kg/m$^2$; the subject has a body mass index greater than 30 kg/M$^2$.

Described herein are methods for the prevention of abnormal body weight gain or reduction of excessive body weight or obesity which comprise administering to a patient that is susceptible to abnormal body weight gain or is overweight or obese, an effective non-toxic dose of O-(3-piperidino-2-hydroxy-1-propyl)-nicotinic amidoxime or a pharmaceutically acceptable acid addition salt thereof.

BGP-15 can be prepared by the process described in e.g. U.S. Pat. No. 4,187,220.

A pharmaceutically suitable acid addition salt of BGP-15 is a salt formed with an inorganic acid such as, for example, hydrochloric acid and sulfuric acid or with an organic acid such as, for example, acetic acid, lacetic acid and tartaric acid. A preferred acid addition salt of O-(3-piperidino-2-hydroxy-1-propyl)nicotinic amidoxime is the dihydrochloride thereof.

A non-toxic dose of BGP-15 or a pharmaceutically suitable acid addition salt thereof is administered to reduce weight gain, reduce the risk of weight gain or reduce the rate of weight gain. This, non-toxic dose of BGP-15 reduces,or prevents, effectively, the abnormal body weight gain or reduces excessive body weight or obesity. In general, the daily dose for an adult person of about 70 kg body weight is 5 mg to 1000 mg of BGP 15 (as dihydrochloride), suitably 50-500 mg of BGP-15.

BGP-15 or a pharmaceutically suitable acid addition salt thereof is administered in form of a conventional pharmaceutical composition containing the active agent and, optionally, one or more pharmaceutically acceptable carrier(s). The pharmaceutical composition may include any dosage form suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as microcrystalline cellulose, lactose, glucose, starch, calcium phosphate etc.; auxiliary substances for tabletting such as magnesium stearate, talc, poly(ethylene glycol), sodium stearyl fumarate, silica etc.; wetting agents such as sodium laurylsulfate, poloxamers etc. as the carrier. Capsules may contain the pure active agent without any carrier, other dosage forms contain, in addition to the active agent, one or more carrier(s).

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propylene glycol, ethanol etc.; preservatives such as methyl p-hydroxybenzoate etc. as the carrier.

Pharmaceutical compositions suitable for parenteral administration consist of sterile solutions of the active ingredients, in general. The sterile solution may contain, in addition to the active agent, pH control agents and osmolarity control agents, preservatives, surfactants etc.

Dosage forms listed above as well as other dosage forms are known per se, see e.g. Remington's Pharmaceutical Sciences, 18th Edition, Mack Publishing Co., Easton, USA (1990).

The pharmaceutical composition contains dosage unit, in general. The daily dose can be administered in one or more portions. The actual dosage depends on many factors and is determined by the doctor.

The pharmaceutical composition is prepared by admixing the active ingredient to one or more carrier(s), and converting the mixture obtained to a pharmaceutical composition in a manner known per se. Useful methods are known from the literature, e.g. Remington's Pharmaceutical Sciences mentioned above.

EXAMPLE 1

Effect of BGP-15 on the Body Weight Gain Induced by Olanzapine or Clozapine

Since it is known that certain antipsychotics induce overweight and later obesity in the treated patients [Ruetsch O. et al., L'Encéphale, 31, 507-16 (2005)], rats treated with olanzapine [2-methyl-4-(4-methyl-1-piperazinyl)-10H-thieno[2,3-b][1,5]-benzodiazepine] or mice treated with olanzapine or clozapine [8-chloro-11-(4-methyl-1-piperazinyl)-5H-dibenzo[b,e][1,4]diazepine] were used as the experimental system for the determination of the effect of BGP-15 on abnormal weight gain.

Groups of female Wistar rats were treated with vehicle (control group) and the agents to be tested for 28 days. Each group consisted of 6 animals fed with normal laboratory chow and tap water ad libitum. The agents to be tested were administered twice daily, at 8 h and 18 h, perorally. The antipsychotic olanzapine was administered in a dose of 1 mg/kg to induce body weight gain. BGP-15 was administered in a dose of 10 mg/kg, alone and together with olanzapine. The oral antidiabetics metformin (100 mg/kg) and rosiglitazone (3 mg/kg) were employed as reference compounds, alone and together with olanzapine. The average starting weight of the animals was 171 g. The weights of the animals at the end of the test on the 28th day are listed in Table 1.

TABLE 1

| Treatment | Body weight (average in the group) in g |
| --- | --- |
| Control | 255 |
| Olanzapine, 1 mg/kg | 330 |
| BGP-15 dihydrochloride, 10 mg/kg | 242 |
| Metformin, 100 mg/kg | 266 |
| Rosiglitazone, 3 mg/kg | 284 |
| Olanzapine 1 mg/kg + BGP-15 dihydrochloride 10 mg/kg | 262 |
| Olanzapine 1 mg/kg + metformin 100 mg/kg | 331 |
| Olanzapine 1 mg/kg + rosiglitazone 3 mg/kg | 359 |

The weight gain of the control group relative to the starting weight during the test period of 28 days can be considered as normal in case of rats. Olanzapine produced high average weight relative to the control group. Treatment with BGP-15 alone reduced the average weight relative to the control group, while treatment with metformin and rosiglitazone, respectively, produced somewhat higher average weight relative to the control group. In the group treated with both olanzapine and BGP-15 dihydrochloride, a very high reduction of the body weight was experienced and nearly the value that characterized the healthy animals (control group) was obtained. Treatment with metformin did not reduce, while treatment with rosiglitazone even increased the weight gain induced by olanzapine in the experimental model.

Groups of female NMRI mice were treated with vehicle (control group) and the agents to be tested for 15 days, perorally. Each group consisted of 10 animals fed with normal laboratory chow and tap water ad libitum. Treatments were performed between 5 and 6 pm, shortly before the dark phase, the primary feeding period of the day. Olanzapine was administered in a dose of 0.5 mg/kg, while clozapine was administered in a dose of 1 mg/kg to induce body weight gain. BGP-15 was administered in a dose of 10 mg/kg, alone and together with olanzapine and clozapine, respectively. Weight of the animals were recorded twice weekly and the increase of the body weight of the animals between the first and 15th days are given in Table 2.

TABLE 2

| Treatment | Body weight gain (average in the group) in g |
| --- | --- |
| Control | 2.98 |
| Olanzapine, 0.5 mg/kg | 3.5 |
| Clozapine, 1 mg/kg | 4.11 |
| BGP-15 dihydrochloride, 10 mg/kg | 2.85 |
| Olanzapine, 0.5 mg/kg + BGP-15 dihydrochloride, 10 mg/kg | 2.33 |
| Clozapine, 1 mg/kg + BGP-15 dihydrochloride, 10 mg/kg | 2.19 |

BGP-15 alone could lower the body weight gain by about 4.4% relative to the control. However, in the groups of the experimental model, BGP-15 could reduce the body weight change relative to the control group by 22% and 26.5%, respectively.

EXAMPLE 2

Effect of BGP-15 on the Body Weight Gain Induced by Risperidone in Rats

The experiments were carried out in eight-week-old female Wistar rats. Each test group consisted of 10 animals fed with normal laboratory chow and tap water ad libitum. The animals were treated with vehicle (control group) and the compounds to be tested for 21 days. In this experimental system, the antipsychotic risperidone was injected subcutaneously once daily in doses of 0.005 and 0.05 mg/kg, respectively to induce body weight gain. BGP-15 dihydrochloride was administered in a dose of 20 mg/kg, perorally, once daily, alone and together with risperidone.

The average starting weight of the animals was 195 g. The weight gains of the animals at the end of the test on the 21st day are listed in Table 3

TABLE 3

| Treatment | Body weight gain (g) |
| --- | --- |
| Control | 27 |
| BGP-15 dihydrochloride 20 mg/kg p.o. | 22.7 |
| Risperidone 0.005 mg/kg s.c. | 39.7 |
| Risperidone 0.05 mg/kg s.c. | 41 |
| Risperidone 0.005 mg/kg s.c. + BGP-15 dihydrochloride 20 mg/kg p.o. | 25.8 |
| Risperidone 0.05 mg/kg s.c. + BGP-15 dihydrochloride 20 mg/kg p.o. | 28.7 |

Both doses of the antipsychotic drug risperidone caused increased body weight gain relative to the control group. BGP-15 alone reduced body weight gain somewhat. However, in both groups of the experimental model, BGP-15 could reduce the body weight change caused by the addition of risperidone.

EXAMPLE 3

Effect of BGP-15 on the Body Weight of Mice that are Genetically Susceptible to Obesity The ob/ob mouse represents a genetic model of obesity, where the mutation of leptin gene, one of the most important satiety hormone, causes the disease. The leptin-deficiency causes both reduced metabolic rate and increased food intake. These mice show a rapid weight gain, the 6 weeks old animals have an average body weight of about 30 g, while the wild type mice at that age have only about 20 g of body weight.

In the test, 6 weeks old, male ob/ob mice were treated orally with 15 mg/kg daily dose of BGP-15 dihydrochloride for 15 days. The weight of the animals were measured weekly. The body weights of the control and BGP-15 treated animals after 15 days treatment are shown in Table 3.

TABLE 3

| Treatment | Body weight gain (grams) |
|---|---|
| Control (vehicle) | 8.73 ± 0.76 |
| BGP-15 diydrochloride, 15 mg/kg | 6.35 ± 0.17 |

As Table 3 indicates, BGP-15 dihydrochloride caused a rather significant reduction in body weight gain in ob/ob mouse model of obesity since the body weight gain of the test group was lower by 27% than that of the control group.

EXAMPLE 4

Effect of BGP-15 on the Body Weight Gain Induced by High Fat Diet in Mice

Test groups of female NMRI mice obtained palatable food that contained 50% fat. In one of the test groups, mice were treated, perorally, with a dose of 20 mg/kg of BGP-15 dihydrochloride, daily. The animals of the control group were fed with conventional mouse food with low fat content. In a further group of mice fed with conventional mouse food, the animals were treated, perorally, with 20 mg/kg of BGP-15 dihydrochloride, daily. The weight of the animals were evaluated weekly for two weeks and body weight changes were calculated. At the beginning of the study, the average weight of the animals was about 26 g. The average body weight gains on the 8th and 15th day of the experiment are shown in Table 4.

TABLE 4

| Treatment | Body weight gain (g) | |
|---|---|---|
| | on day 8 | on day 15 |
| Control (conventional diet) | 1.97 | 2.47 |
| BGP-15 dihydrochloride 20 mg/kg p.o. (conventional diet) | 2.01 | 2.48 |
| Palatable high fat diet | 3.65 | 5.37 |

TABLE 4-continued

| Treatment | Body weight gain (g) | |
|---|---|---|
| | on day 8 | on day 15 |
| Palatable high fat diet + BGP-15 dihydrochloride 20 mg/kg p.o. | 2.48 | 2.67 |

From Table 4 it can be seen that palatable high fat diet resulted in a very high body weight gain relative to the control group, however, BGP-15 treatment almost completely blocked the effect of high fat diet. BGP-15 treatment alone had no significant effect on body weight gain in case of conventional diet.

In the Examples it was shown that obesity developed in different experimental models could be effectively reduced by treatment with BGP-15.

A number of embodiments of the invention have been described. Nevertheless, it will be understood that various modifications may be made without departing from the spirit and scope of the invention. Accordingly, other embodiments are within the scope of the following claims.

What is claimed is:

1. A method for reducing body weight gain or the rate of body weight gain in a patient in need thereof, the method comprising administering to the patient an effective non-toxic dose of O-(3-piperidino-2-hydroxy-1-propyl)-nicotinic amidoxime or a pharmaceutically acceptable acid addition salt thereof;

wherein the patient is not suffering from diabetes mellitus, is not being treated with exogenous insulin, and is not being treated with any other anti-diabetic or anti-hyperlipidemic agents.

2. The method of claim 1 wherein the patient has a body mass index greater than 25 kg/m$^2$.

3. The method of claim 1 wherein the patient has a body mass index greater than 30 kg/m$^2$.

* * * * *